(12) United States Patent
Charukhchian

(10) Patent No.: US 7,896,848 B2
(45) Date of Patent: Mar. 1, 2011

(54) OSTOMY TUBE DEVICE, OSTOMY PLACEMENT KIT AND METHOD FOR AN OSTOMY TUBE PLACEMENT

(76) Inventor: Samvel Artavazovich Charukhchian, Decatur, GA (US)

( * ) Notice: Subject to any disclaimer, the term of this patent is extended or adjusted under 35 U.S.C. 154(b) by 0 days.

(21) Appl. No.: 11/170,903

(22) Filed: Jun. 29, 2005

(65) Prior Publication Data

US 2007/0016172 A1  Jan. 18, 2007

(51) Int. Cl.
  *A61M 5/32* (2006.01)
  *A61M 31/00* (2006.01)
(52) U.S. Cl. ........................ 604/175; 604/500
(58) Field of Classification Search ............. 607/40, 607/41, 133; 600/120; 128/4, 6; 606/108; 604/97, 104, 175, 178, 247, 270, 516, 523, 604/533, 535
  See application file for complete search history.

(56) References Cited

U.S. PATENT DOCUMENTS

| | | | |
|---|---|---|---|
| 534,032 A * | 2/1895 | Clymer | 14/6 |
| 4,573,576 A * | 3/1986 | Krol | 206/471 |
| 4,666,433 A | 5/1987 | Parks | |
| 4,795,430 A * | 1/1989 | Quinn et al. | 604/102.02 |
| 5,007,900 A * | 4/1991 | Picha et al. | 604/106 |
| 5,074,846 A | 12/1991 | Clegg | |
| 5,084,014 A * | 1/1992 | Picha et al. | 604/500 |
| 5,112,310 A | 5/1992 | Grobe | |
| 5,259,367 A | 11/1993 | Kirby | |
| 5,330,488 A * | 7/1994 | Goldrath | 606/148 |
| 5,356,391 A | 10/1994 | Stewart | |
| 5,391,159 A | 2/1995 | Hirsch | |
| 5,555,898 A | 9/1996 | Suzuki | |
| 5,807,314 A * | 9/1998 | Ross et al. | 604/500 |
| 6,039,714 A | 3/2000 | Cracauer | |
| 6,093,479 A | 7/2000 | O'Hara | |
| 6,402,722 B1 | 6/2002 | Snow | |
| 6,527,748 B1 * | 3/2003 | Suzuki | 604/171 |
| 6,673,058 B2 | 1/2004 | Snow | |
| 6,765,122 B1 | 7/2004 | Stout | |
| 6,808,519 B2 * | 10/2004 | Fanelli et al. | 604/523 |
| 6,907,992 B2 | 6/2005 | McMichael | |

(Continued)

OTHER PUBLICATIONS

Jeffrey L. Ponsky. Percutaneus Endoscopic Gast-rostomy, Gastrointestinal Endoscopy, 1981, V27, #1, p. 9-11.

(Continued)

*Primary Examiner*—Kevin C Sirmons
*Assistant Examiner*—William Carpenter

(57) ABSTRACT

An ostomy tube device comprises a hollow flexible tube with internal retention member, a tapered hollow cannula and a pull-loop member forming leading and rear pole loop when positioned through the tapered cannula. The hollow flexible tube folded over the rear pole loop and squeezed into the lumen of the tapered cannula provides a releasable attachment. An ostomy placement kit includes an ostomy tube device, an external retention member, a needle, a flexible guide wire, a wire-loop device and a tubular device for external retention member delivery. The flexible guide wire is passed through an endoscope into the hollow organ, is grasped with the wire-loop device, and is pulled through the abdominal wall. The ostomy tube device attached to guide wire is passed and positioned through the abdominal wall. Tapered cannula is pulled off the hollow flexible tube and the external retention member is positioned over using the tubular device.

26 Claims, 9 Drawing Sheets

U.S. PATENT DOCUMENTS 6,997,900 B2 * 2/2006 Weststrate et al. .......... 604/104
7,127,295 B2 * 10/2006 Evans ........................ 607/40
2005/0020875 A1 * 1/2005 Delegge .................... 600/101

OTHER PUBLICATIONS

David E. Larson. Percutaneous Endoscopic Gastrostomy Mayo Clinic Proc, 1983, V58, Feb, pp. 103-107.

Bard Catalog Products for Endoscopy 2003 p. 5-6 Billerica, MA USA.

Wilson-Cook Medical Catalog 2005 Product Gide p. 181 Winston-Salem, NC, USA.

Boston-Scientific Catalog Products for Endoscopy 2005 p. 51 Natick, MA USA.

Kimberly-Clark MIC PE6 Web Site http://www.bmed.com/products/eftmain.htm.

In: Feeding tube use has shifted, technique's developers say. Posted Mar. 26, 2005 9:23 AM at : http://www.usatoday.com/news/nation/2005-03-26-feeding-tubes_x.htm.

In: Digestive Disease Statistics at http://digestive.niddk.nih.gov/statistics/statistics.

Charukhchian, Samvel. Percutaneus Ostomy (Gastrostomy) Tube, Percutaneus Ostomy Kit, and Methodof their use. Disclosure Document # 534032 Filed with Patent Office on Jun. 30, 2003.

Document # 3 is not prior art reference. It is proof of conception of present invention # 11/170,903 filed with US Patent Office Disclosure Document Program.

* cited by examiner

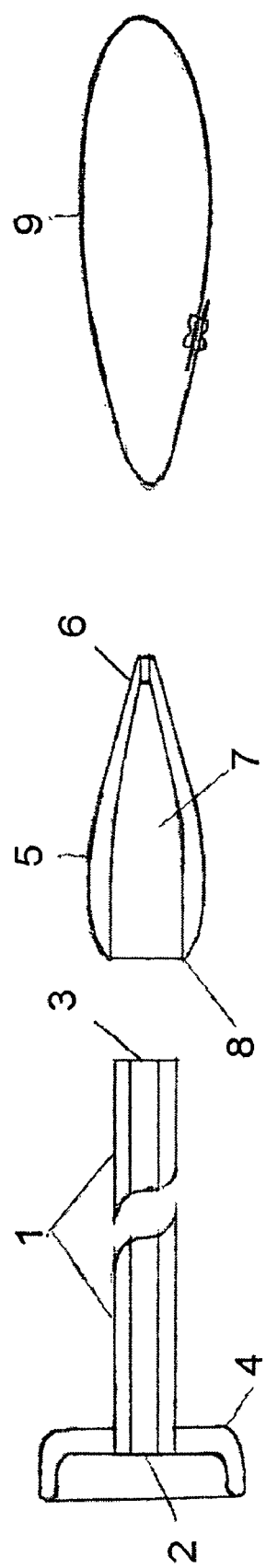

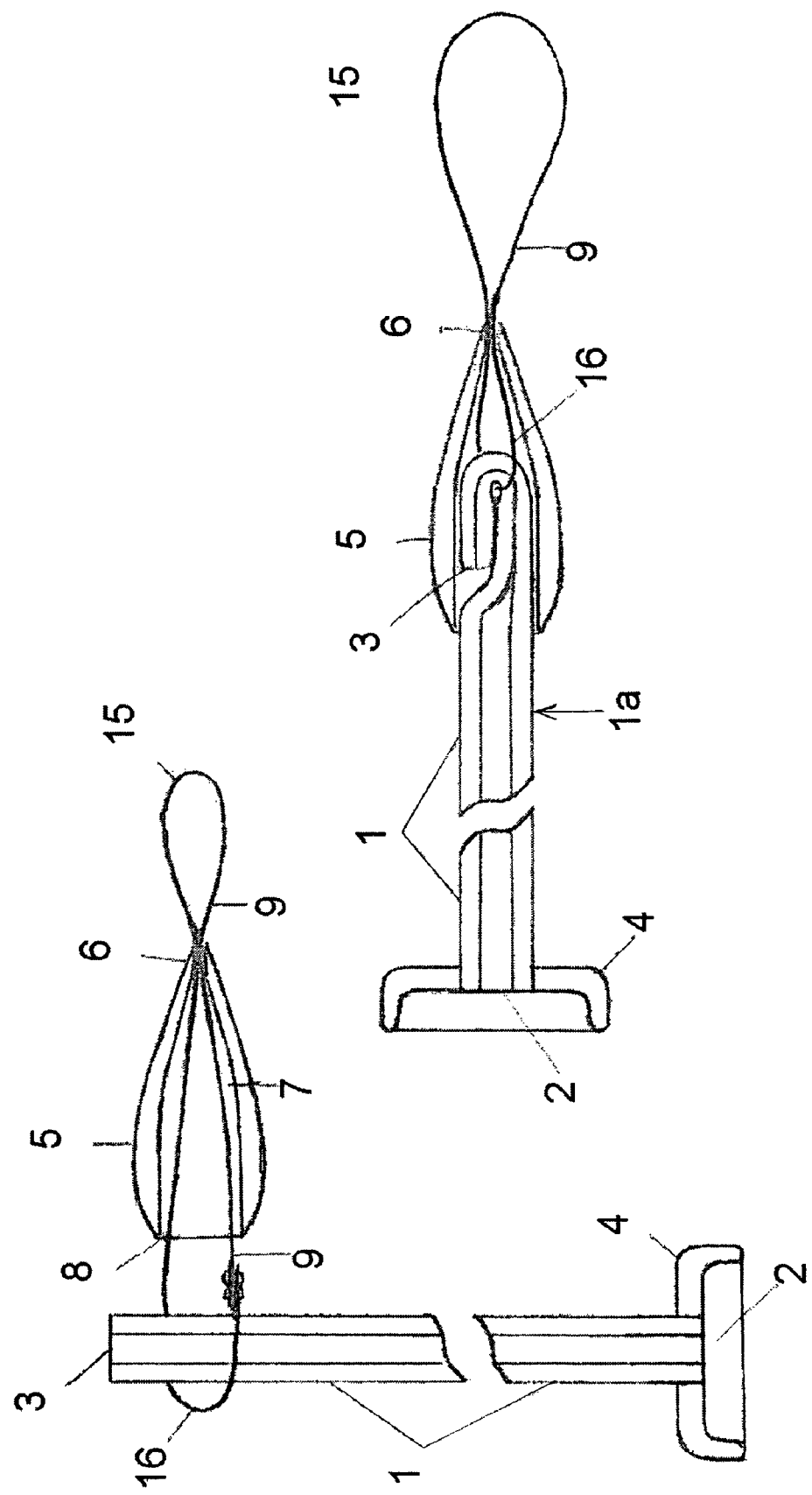

OSTOMY TUBE DEVICE, OSTOMY PLACEMENT KIT AND METHOD FOR AN OSTOMY TUBE PLACEMENT

CROSS-REFERENCE TO RELATED APPLICATIONS

NOT APPLICABLE

FEDERALLY SPONSORED RESEARCH

NOT APPLICABLE

SEQUENCE LISTING OR PROGRAM

NOT APPLICABLE

TECHNICAL FIELD

This invention relates to medical devices and methods, more particularly, to improved ostomy tube devices, ostomy placement kits and to methods for an ostomy tube placement.

BACKGROUND OF THE INVENTION

An ostomy placement as, for example, gastrostomy, jejunostomy, colostomy, ileostomy is utilized in medical profession for feeding patients with impaired swallowing but intact gut function as well as for decompression of overdistended hollow organs. While it is possible to create the ostomy by surgical procedure, recently less invasive endoscopic or fluoroscopic methods of percutaneous ostomy tube placement are widely employed. The percutaneous endoscopic gastrostomy (PEG) tube placement is one of the most commonly used prototypes of the ostomy placement.

The percutaneous endoscopic gastrostomy (PEG) tube placement, as it is described in U.S. Pat. No. 6,808,519, "involves introduction of a gastroscope into the stomach, while desired site where the stoma is to be created is indicated from above by depressing the abdomen. A sheathead needle punctures the abdominal wall and enters the stomach, creating the stoma. The needle is removed and a looped insertion wire is introduced through the sheath where it is grasped by a snare deployed from the working channel of the gastroscope. Once it is captured, the insertion wire is pulled into the channel of the gastroscope. The gastroscope is then withdrawn from the patient via the oral cavity, pulling the wire with it. In the standard Ponsky method (or "pull" method), the distal loop of a percutaneous gastrostomy feeding tube is coupled to the insertion wire loop exiting the patients mouth. With the insertion wire now tethered to the gastrostomy feeding tube, the endoscopist then retracts the insertion wire exiting the stoma, thereby pulling the gastrostomy feeding tube into the patient's mouth and on toward the stomach. The tapered dilator portion aids in allowing the gastrostomy feeding tube to pass through the stoma. Once the tube has been properly positioned with the end cap snugd against the internal wall of the stomach, the dilator portion of the gastrostomy feeding tube is cut away." This technique was described initially by Jeffrey L. Ponsky and Michael W. L. Gauderer in "Percutaneous endoscopic gastrostomy: a nonoperative technique for feeding gastrostomy", Gastrointestinal Endoscopy, Vol. 27, N0 1, 1981, pp 9-11. In addition to above steps in the Ponsky and Gauderer references cited above, "another rubber bumper is prepared and is positioned on the catheter (feeding tube) as it emerges from the abdominal wall". "Rubber bumper" placed over the feeding tube, also known as external retention member, is slidably movable and frictionally retained over feeding tube. Once the feeding tube is secured in place, the Y-port adapter is connected to it.

Various types of gastrostomy tube devices were employed for percutaneous insertion by above "pull" method. Most gastrostomy tube devices, including commercially available from Wilson-Cook Medical Inc., Winston-Salem, N.C. or Boston Scientific Corporation, Watertown, Mass., comprise a tubular body having an internal retention member secured at one end, a dilator portion integrally attached at an opposite end, and a pull loop integrally formed and projecting outwardly from the dilator tip.

The percutaneous gastrostomy tube devices are preferably supplied in a kit form additionally including a guide wire, a needle catheter, an external retention member having a bore, and a snare.

There are problems associated with all three components (device, kit, method) of the above prior art technique. For example:

1. Commercially available gastrostomy tube devices with the dilator portion integrally attached to tubular body require sharp devices such as scissors or knife to cut away the dilator portion or the pull loop.

2. A gastrostomy tube device described in the Ponsky and Gauderer references cited above requires the time consuming assembly of several separate components in preparation for the operation. This also requires scissors or knife to cut off suture placed through the end of feeding tube. Alternatively time and effort are required to untie abovementioned suture from "guide-wire", pull off cannula, and remove stitch passed through the end of feeding tube. Additionally placing the suture through the end of the feeding tube may result in partial or complete cutting through that end the feeding tube. This is especially true in cases of significant pull forces used.

3. The external retention member of the prior art is difficult to engage over the end of gastrostomy tube because of a smaller size of the bore.

4 The external retention member of the prior art is difficult to move along hollow flexible tube for 30-60 cm because of sliding friction.

5. The external retention member of the prior art is difficult to position accurately at abdominal surface level because of sliding friction 6. The guide-wire in the methods of the prior art is first pulled through the abdominal wall access to the mouth, to be then pulled from mouth to and through the abdominal wall access.

7. Use of the snare or any other grasping device suitable for passing through an endoscope is associated with several problems:

a) time and effort are required to advance the snare through about 130-150 cm long working channel of endoscope;

b) time and effort are required to remove the snare from about 130-150 cm long working channel of endoscope;

c) capturing of the guide-wire with a snare is complex maneuver requiring coordination of simultaneous movement of endoscope and snare in different direction;

d) an additional assistant is used to open and close the snare;

e) a snare occupies a lot of space in percutaneous gastrostomy kits;

i) a snare adds a cost to percutaneous gastrostomy kits.

Present invention has various advantages over and addresses several of the shortcomings of previously described techniques:

1. Provides secure and releasable attachment between the hollow flexible tube, the pull-loop member, and the tapered cannula. This attachment is strong enough and, at the same time, easy to disengage.

2. Eliminates the need of sharp devices such as scissors or knifes to cut the hollow flexible tube, or a pull-loop member to release the hallow flexible tube.

3. External retention member coupled with tubular device is easy to engage over the end of the hollow flexible tube.

4. External retention member coupled with tubular device is easy to move along the hollow flexible tube.

5. Use of a tubular device with side opening provides an accurate positioning of the external retention member.

6. Use of a wire-loop device eliminates steps of pulling the guide-wire through abdominal wall access to the mouth.

7. Use of the wire-loop device eliminates complex step of capturing the flexible guide wire by snare device.

8. Use of the wire-loop device eliminates the need of using the snare or any other grasping device suitable for passing through an endoscope, whereby:

a) saves time and effort required to advance the snare through about 130-150 cm long working channel of endoscope, b) saves time and effort required to remove the snare from about 130-150 cm long working channel of endoscope, c) eliminates the need of the assistant to open and close the snare, d) saves the space in percutaneous gastrostomy kits, e) reduces the cost to percutaneous gastrostomy kits, These and further objects and advantages of the present invention will become more apparent upon reference to the following drawings, ensuing description and appended claims.

SUMMARY OF THE INVENTION

The present invention provides an improved ostomy tube device, an improved ostomy placement kit and an improved method for an ostomy tube placement.

In accordance with the present invention, an ostomy placement kit in addition to an external retention member, a needle and a flexible guide wire, includes in different combinations: an ostomy tube device, a wire-loop device and a tubular device for delivering the external retention member over the ostomy tube device.

An ostomy tube device of the present invention comprise a hollow flexible tube with internal retention member secured at a first end and a tapered hollow cannula with a pull-loop member releasably attached to a second end. The tapered cannula has a wide portion ending by a wide end and a tapered portion ending by a tapered end, and a lumen open on both ends. The pull-loop member when positioned through the lumen of the tapered cannula forms a leading pole loop and a rear pole loop. The second end of the hollow flexible tube is folded over the rear pole loop and squeezed into the lumen of the wide portion of the tapered cannula, pulled by the rear pole loop. This configuration provides a secure and easy releasable attachment between the pull-loop member, the tapered cannula and the hollow flexible tube. In accordance with the present invention, the wire-loop device has a mid-portion rod with a wire-loop attached to one end and a handle attached to the other end. In further accordance with the present invention, the tubular device is constructed as a tube of about 3-5 cm from non collapsible, hard material with a lumen slightly bigger than the diameter of the hollow flexible tube of the ostomy tube device. The tubular device included in the ostomy placement kit, has the external retention member positioned over its leading end. The tubular device may have an additional opening on a side, communicating with its lumen.

In accordance with the present invention, a method for an ostomy tube placeman includes the following steps: (i) advancing an endoscope through a body opening into a lumen of a desired hollow organ, (ii) introducing a needle into the lumen of the desired hollow organ through an abdominal wall, (iii) passing a wire-loop of a wire-loop device through the needle into the lumen of the hollow organ, (iv) passing a flexible guide wire through the endoscope into the lumen of desired hollow organ, (v) positioning a second end of the flexible guide wire through the wire-loop of the wire-loop device, (vi) grasping the flexible guide wire by the wire-loop of the wire-loop device, (vii) pulling the second end of the flexible guide wire grasped by the wire-loop from the lumen of the hollow organ out through the abdominal wall, (viii) withdrawing the endoscope out of body opening and leaving the first end of the flexible guide wire extending out of body opening, (ix) securing the first end of the flexible guide wire to the leading pole loop of the ostomy tube device, (x) passing the ostomy tube device through the body opening, the lumen and the hollow organ wall, and the abdominal wall by pulling the flexible guide wire until the leading pole loop with the attached tapered cannula and the hollow flexible tube extend out of the abdominal wall and an internal retention member abuts against the inner surface of the hollow organ, (xi) releasing a second end of the hollow flexible tube from the attachment between the leading pole loop, the hollow flexible tube, and the tapered cannula by pulling apart the hollow flexible tube and the tapered cannula of the ostomy tube device, (xii) passing an external retention member positioned on a tubular device over the second end the hollow flexible tube and along the hollow flexible tube, (xiii) holding the hollow flexible tube, passed trough the lumen of the tubular device, against the tubular device by a finger through an additional opening on a side of the tubular device while removing the external retention member from the tubular device, (xiv) pulling off the tubular device from the hollow flexible tube.

BRIEF DESCRIPTION OF THE DRAWINGS

These and further features of the present invention will be apparent with reference to the following description and drawings, wherein:

FIG. 1A is a sectional view of disassembled ostomy tube device of the present invention including a hollow flexible tube, a tapered cannula, and a pull-loop member of first embodiment.

FIG. 2A is a sectional view showing schematic relation between the hollow flexible tube, the tapered cannula, and the pull-loop member in process of assembling the ostomy tube device of present invention.

FIG. 2B is a sectional view showing schematic relation between the hollow flexible tube, the tapered cannula, and the pull-loop member of assembled ostomy tube device of the present invention.

DETAILED DESCRIPTION OF THE INVENTION

Figure 1B:
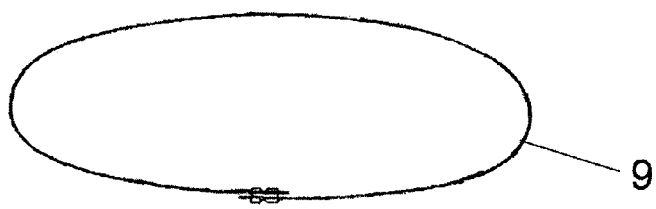
FIG. 1B is a schematic view of the pull-loop member of first embodiment.

An ostomy tube device according to the present invention, as shown in FIG. 1A, includes a hollow flexible tube 1 with a collapsible internal retention member 4 secured at a first end 2, a tapered cannula 5 and a pull-loop member 9.

The hollow flexible tube 1 has a first end 2, a second end 3 and a lumen opened at both ends. Also, the hollow flexible tube 1 has a collapsible internal retaining member 4 surrounding the first end 2 and being secured thereto.

The collapsible retention member 4 may be either flat, having different configuration, or have dome shape, or mushroom shape, or constructed as inflatable balloon, or have any other construction. Generally speaking a collapsible internal retention member of any shape can be used in conjunction with this invention. The collapsible internal retaining member 4 may be secured to the hollow flexible tube 1 by heat sealing, adhesives, sonic bonding, integrally formed with the hollow flexible tube 1, or attached to it.

Spacing indicia are provided along the hollow flexible tube to enable location of the device during installation, and during use.

The tapered cannula 5 has a wide portion ending by a wide end 8 and a tapered portion ending by a tapered end 6. Also, the tapered cannula 5 has a lumen 7 opened on both ends. The lumen 7 of the wide portion of tapered cannula 5 is sized to accommodate folded twice and collapsed hollow flexible tube 1. The lumen 7 of the tapered portion of tapered cannula 5 is sized to slidably accommodate the pull-loop member 9 passed through. The tapered cannula is made from semi-rigid, yet flexible, or rigid material.

The pull-loop member 9 is constructed from a flexible thread. The flexible thread is preferably made from a metal wire such as medical stainless steel wire, but can be made from any synthetic polymer material, as well as natural materials such as silk, and their combinations.

In first embodiment of the pull-loop member 9 a first and a second ends of the flexible thread are fastened together forming O shape closed loop as also shown on FIG. 1B.

Figure 1C:
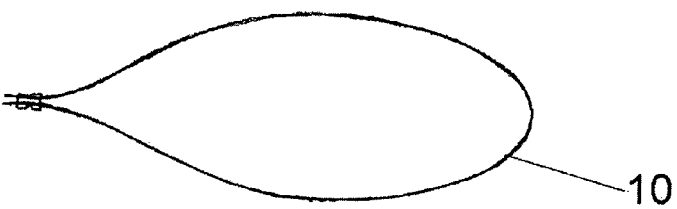
FIG. 1C is a schematic view of a pull-loop member of a tear droop shape.

Alternatively, the first and the second ends of the flexible thread are fastened together forming a tear droop shape closed loop as in the pull-loop member 10 shown on FIG. 1C.

Figure 1D:
FIG. 1D is a schematic view of O-ring uninterrupted pull-loop member.

Also, the pull-loop means can be constructed as O ring from uninterrupted flexible thread as in the pull-loop member 11 shown on FIG. 1D.

Figure 1E:
FIG. 1E is a schematic view of a pull-loop member with two closed loops separated by a segment of the midportion of the flexible thread.

In another embodiment of the pull-loop member the first and the second ends of the flexible thread are fastened to a midportion of the flexible thread separately and apart one from the other forming the pool-loop member 12 with two closed loops separated by a segment of the midportion of the flexible thread shown on FIG. 1E.

Figure 1F:
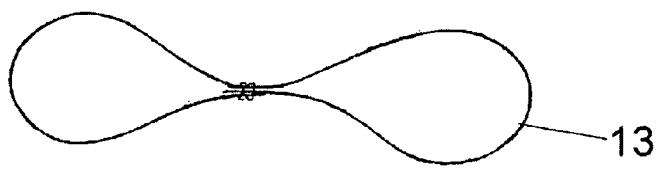
FIG. 1F is a schematic view of a pull-loop member with two adjacent closed loops.
Figure 1G:
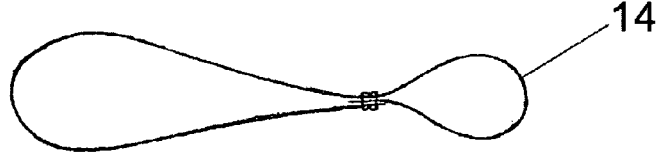
FIG. 1G is a schematic view of a pull-loop member with two adjacent closed loops having different size.

Alternatively, the first and the second ends of the flexible thread are fastened together and to the midportion of the flexible thread forming the pool-loop member with two closed loops not separated by the segment of the midportion of flexible thread. Closed loops in such embodiment may have approximately equal size as in the pull-loop member 13 shown on FIG. 1F, or one loop may be bigger then the other such as in the pull-loop member 14 shown on FIG. 1G.

Figure 1H:
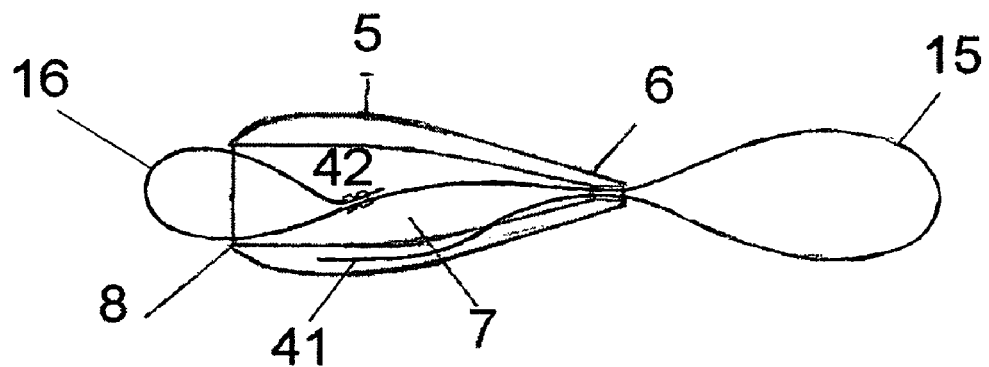
FIG. 1H is a sectional view of the tapered cannula with a pool-loop member positioned through its lumen with a first end of a flexible thread imbedded into the tapered cannula.

FIG. 1H illustrates the pull-loop member constructed from the flexible thread having the first end 41 imbedded into the wall of the tapered cannula 5, and the second end 42 fastened to midportion of the flexible thread forming a rear pole loop 16. The flexible thread is passed through the lumen 7 of the tapered cannula 5 so that midportion of flexible thread extends from the tapered end 6 of the tapered cannula 5 forming a leading pole loop 15 while the rear pole loop 16 extends out of tapered cannula through the wide end 8.

Figure 1K:
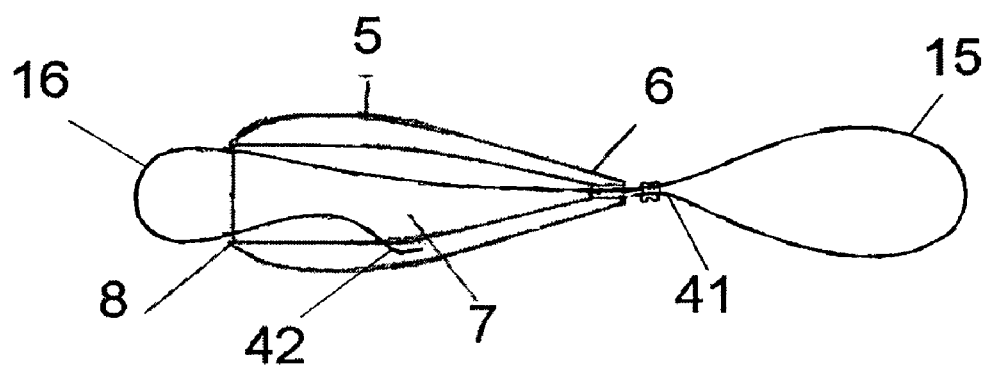
FIG. 1K is a sectional view of the tapered cannula with a pool-loop member positioned through its lumen with a second end of the flexible thread imbedded into the tapered cannula.

FIG. 1K illustrates the pull-loop member constructed from the flexible thread having the second end 42 imbedded into the wall of the tapered cannula 5 and the first end 41 fastened to midportion of the flexible thread forming the leading pole loop 16. The flexible thread is passed through the lumen 7 of the tapered cannula 5 so that midportion of flexible thread extends from the wide end 8 of the tapered cannula 5 forming the rear pole loop 16 while the leading pole loop 15 extends out of tapered cannula through the tapered end 6.

Figure 1L:
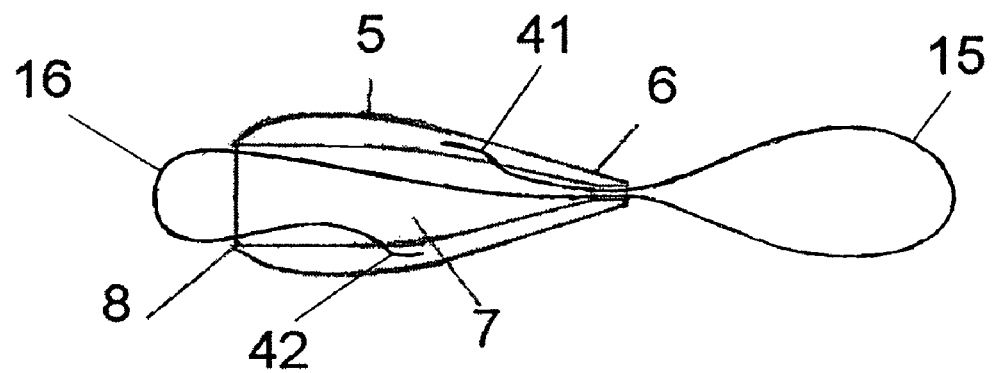
FIG. 1L is a sectional view of the tapered cannula with a pool-loop member positioned through its lumen with the first and the second ends of the flexible thread imbedded into the tapered cannula.

FIG. 1L illustrates the pull-loop member constructed from the flexible thread having the first end 41 and the second end 42 imbedded into the wall of the tapered cannula 5. The flexible thread is passed through the lumen 7 of the tapered cannula 5 so that midportion of flexible thread extends from the tapered end 6 of the tapered cannula 5 forming the leading pole loop 15 and from the wide end 8 of tapered cannula 5 forming the rear pole loop 16.

FIG. 2A shows the pull-loop member 9 passed through the lumen 7 of the tapered cannula 5 so that part of the flexible thread extends from the tapered end 6 of the tapered cannula 5 forming the leading pole loop 15, while other part of the flexible thread extends from the wide end 8 of the tapered cannula 5 forming the rear pole loop 16. Similarly, the pull-loop member 10, or 11, or 12, or 13, or 14 depicted in FIGS. 2B-2G, when passed through the lumen 7 of the tapered cannula 5, form the leading pole loop 15 extending from the tapered end 6 of the tapered cannula 5 and the rear pole loop 16 extending from the wide end 8 of the tapered cannula 5. While in further disclosure of the invention we will refer to the pull-loop member 9 all said will be equally applicable to all described above constructions of the pull-loop member.

In the process of assembling the ostomy tube device of present invention, as shown in FIG. 2A, the second end 3 of the hollow flexible tube 1 is positioned through the rear pole loop 16 extending out of the wide portion of the tapered cannula 8 through the wide end 8. Pulling the tapered cannula 5 and the leading pole loop 15 apart, moves the rear pole loop 16 into the lumen 7 of wide portion of the tapered cannula 5. The second end 3 of the hollow flexible tube 1 folds over the rear pole loop 16 and squeezes into the lumen 7 of the wide portion of the tapered cannula 5 pulled by the rear pole loop 16. Generally speaking, the hollow flexible tube 1 of any given diameter, when folded and squeezed, will fit into about the similar size lumen 7 of wide portion of tapered cannula 5. Preferably, assembling of the ostomy tube devices of the present invention, as described above, will be done by manufacturer, while an operator, as a physician, will use already assembled device.

FIG. 2B illustrates the ostomy tube device (1a) of the present invention in assembled configuration. As shown in this figure, the second end 3 of the hollow flexible tube 1 is folded over the rear pole loop 16 and squeezed into the lumen 7 of the wide portion of the tapered cannula 5 pulled by the rear pole loop 16. This configuration provides a secure and releasable attachment between the pull-loop member 9, the tapered cannula 5 and the hollow flexible tube 1. This attachment is strong enough to overcome resistance forces on the ostomy tube device while it is pulled by the leading pole loop 15 through a lumen and a wall of a hallow organ (as, for example, stomach) and an abdominal wall. The second end 3 of the hollow flexible tube 1 is easy to disengage from the attachment with the pull-loop means 9 and the tapered cannula 5 by simply pulling apart the hallow hollow flexible tube 1 and the tapered cannula 5. Approximately 1 to 3 cm (preferably about 2 cm) of the hollow flexible tube 1 from the second end 3 folded over the rear pole loop 16 is enough to provide strong and, at the same time, easy releasable attachment.

Possibility to release the hollow flexible tube 1 from the attachment with the tapered cannula 5 and the pull-loop member 9 eliminates the need of sharp devices as scissors, knifes, cutting pliers to cut the hollow flexible tube 1, or a pull-loop member 9 to release said hallow flexible tube as was done in prior art.

Figure 3A:
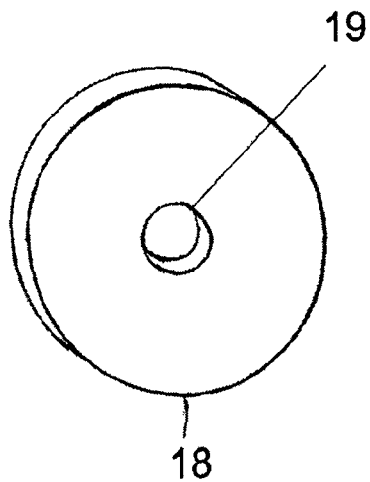
FIG. 3A is a perspective schematic view of an external retention member having a disk configuration.
Figure 3B:
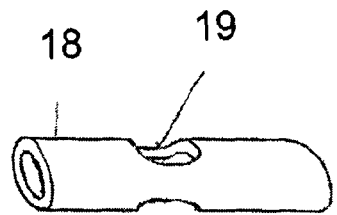
FIG. 3B is a perspective schematic view of an external retention member having a tubular configuration.
Figure 3C:
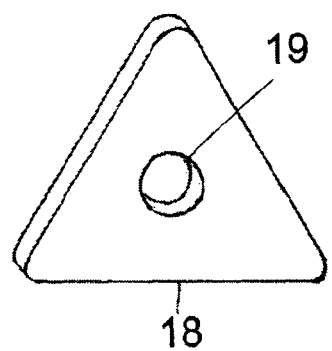
FIG. 3C is a perspective schematic view of an external retention member having a triangular configuration.

FIGS. 3A-3C show external retention members 18 of discoid, tubular, and triangular shape, respectively. Any such external retention member 18 has a bore 19 at about midportion. The bore 19 is sized slightly smaller than outer diameter of the hollow flexible tube 1 of the ostomy tube device of present invention. This size difference allows the bore 19 to accommodate and frictionally retain the hollow flexible tube 1. A size difference of about 10-20 mils is employed in some prior art to provide friction fit between external retention members and hollow flexible tube. However, in prior art this size difference also causes sliding friction when external retention member is moved along hollow flexible tube for 30-60 cm from a second end 3 of hollow flexible tube to its final position against abdominal wall outer surface. Also in prior art this size difference makes it difficult to engage an initial segment of a second end 3 of hollow flexible tube 1 through smaller sized bore 19 of external retention member 18. In one technique grasping forceps are passed through bore 19, grasp second end 3 of hollow flexible tube 1 and pulls pull it back through bore 19. In other technique a tapered dilator integrally attached to a hollow flexible tube is used to engage an initial segment of the hollow flexible tube through smaller sized bore of external retention members. Later technique requires first to cut off a distal wire loop from tapered dilator, and then, when external retention members is appropriately positioned over the hollow flexible tube, to cut off tapered dilator from the hollow flexible tube. These drawbacks of prior art are overcome by employment of a tubular device 20 for delivering the external retention member 18 over the hollow flexible tube described further.

A tubular device of this invention is constructed as a tube of about 3-5 cm having a leading end, a second end and a lumen opened at both ends. The diameter of the lumen of the tubular device is sized slightly bigger then the diameter of the hollow flexible tube 1 of the ostomy tube device. Size difference of about 0.5 mm allows to pass the tubular device over the second end 3 of hollow flexible tube 1, and further along the hollow flexible tube 1 without substantial resistance.

The tubular device is made from non-collapsible, hard enough material as metal or plastic, or composite materials, or their combination to sustain elastic pressure of the external retention member 18 positioned over it without deformity of its lumen.

Figure 3D:
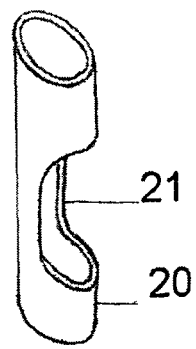
FIG. 3D is a perspective schematic view of a tubular device of the present invention having an additional opening on a side.

FIG. 3D shows another embodiment the tubular device 20, having an additional opening 21 on a side, communicating with its lumen. This additional opening 21 is big enough to accommodate one or more fingers of operator.

Figure 3E:
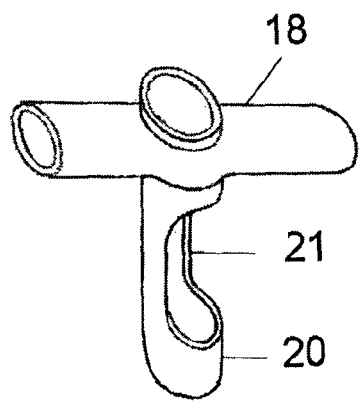
FIG. 3E is a perspective schematic view of the external retention member positioned over the tubular device according to the present invention.

FIG. 3E illustrates the external retention member 18 positioned over the leading end of the tubular device 20. Preferably, assembling of the external retention member 18 and the tubular device 20 will be done by a manufacturer, while an operator, as a physician will use already assembled device. In process of assembly leading end of the tubular device is pushed through the bore of the external retention member. This process can be facilitated by using a cylindrical member with a tapered end positioned through the lumen of the tubular device 20 so that tapered end extends from leading end of the tubular device 20.

Figure 3F:
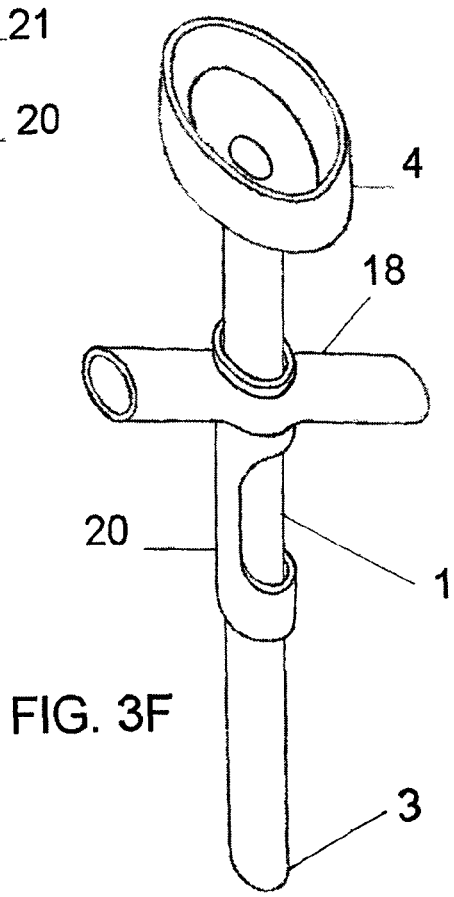
FIG. 3F is a perspective schematic view of the external retention member and the tubular device assembly passed over the hollow flexible tube according to the present invention.

FIG. 3F shows external retention member 18 positioned over the leading end of the tubular device 20 passed over the hollow flexible tube 1 of the ostomy tube device. As was clarified earlier, external retention member 18 positioned over the leading end of the tubular device 20 will pass over the second end 3 of the hollow flexible tube 1 and further along the hollow flexible tube 1 without difficulty or substantial resistance. The additional opening 21 of the tubular delivery device 20 will allow operator to hold securely the hollow flexible tube 1, passed through the lumen of said tubular device 20, against said tubular device 20 using as few as two or three finger. This technique will prevent displacement of the tubular device 20 from the elected place along the hollow flexible tube 1 when the external retention member 18, positioned over the tubular device 20, and the tubular device 20 are pulled apart to remove the external retention member 18 from the tubular device 20. As a result, this technique will allow accurate positioning of the external retention member 18 in elected place along the hollow flexible tube 1 close to the abdominal wall outer surfaces.

A means for delivering the external retention member to desired position over said hollow flexible tube, having a leading end, a second end and a lumen opened at both ends of the means, can be constructed in any shape and configuration provided that at least at one of its end, such as a leading end, the means will be non-collapsible enough to provide, when positioned through said bore of the external retention member, the lumen having size slightly bigger then the diameter of the hollow flexible tube 1 of the ostomy tube device. The means may have one or plurality side openings or splits of any configuration and size, communicating with the lumen of the means. Said openings or splits may or may not extend to one or both ends of the means as long as the lumen of the means with the external retention member positioned over the end, for example, the leading end will be slightly bigger then the diameter of the hollow flexible tube of the ostomy tube device. The tubular device of present invention is one of embodiments of said means for delivering the external retention member to desired position over said hollow flexible tube.

Figure 4A:
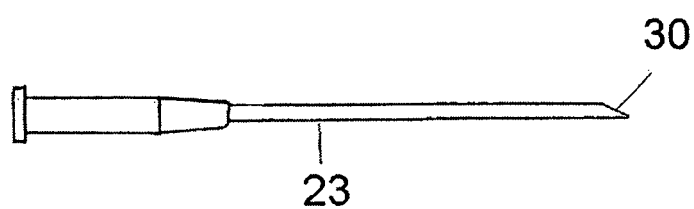
FIG. 4A is an external view of a needle.

FIG. 4A shows a needle 23 having a first end 30 that is placed into a lumen of a hallow hollow organ through an abdominal wall, a second end remaining outside of abdominal wall and a lumen open at both ends. While length and diameter of such a needle can vary, 16 or 18 gauge 8-10 cm needles are preferable. In prior art such needles were mainly used to place guide wire through abdominal wall into the lumen of hollow organ.

Figure 4B:
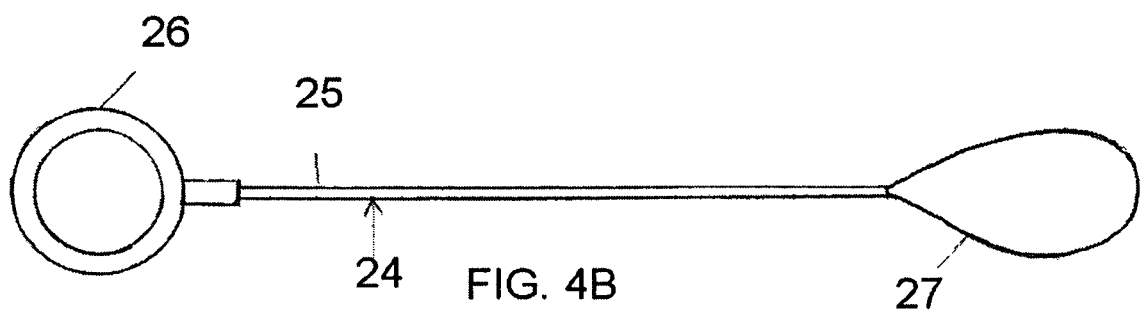
FIG. 4B is an external view of a wire-loop device of the present invention.

FIG. 4B illustrates a wire-loop device 24 having a midportion rod 25, with a wire-loop 27 attached to one end and a handle 26 attached to the other end.

Figure 4C:
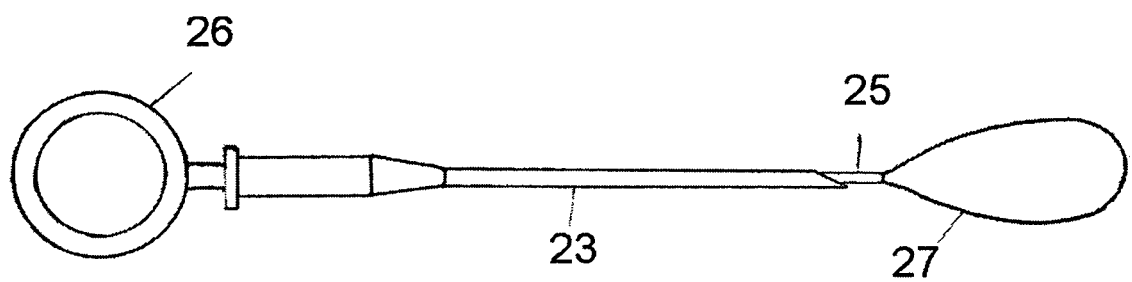
FIG. 4C is an external view of the wire-loop device of the present invention passed through the needle.

The midportion rod 25 and the wire-loop 27 are sized in a diameter to be able to pass trough the lumen of the needle 23, as is shown on FIG. 4 C. Additionally, the midportion rod 25 is sized in length about the length of the needle 23 to allow the wire-loop 27 to extend out of the first end 30 of the needle 23 when the midportion rod 24 is completely engaged in the lumen of the needle 23. When passed through the lumen of the needle 23 placed through abdominal wall into the lumen of hollow organ, the wire-loop device 24 opens and can grasp the end of a flexible guide wire, and pull it through the hollow organ and the abdominal wall outside of body. To grasp the end of the flexible guide wire, the handle 26 of the wire-loop device 24 is pulled away from the needle 23 pulling the wire-loop 27 inside the lumen of the needle 23, of about 16 or 18 gauge, until flexible guide wire 28 is pressed against the first end 30 of the needle 23. Rotating the plane of open wire-loop 27 by means of the handle 26 remaining outside of subjects body can help in positioning the end of the flexible guide wire 28 through the open wire-loop 27.

FIGS. 5A-5F illustrate the method of an ostomy tube placement of present invention. It is to be noted, that while FIGS. 5A-5F illustrate an ostomy tube placement through stomach 31 and abdominal wall 33, also known as percutaneous gastrostomy tube placement, the method disclosed herein can be used in other areas of body, such as, for example, jejunostomy, colostomy, ileostomy.

Figure 5A:
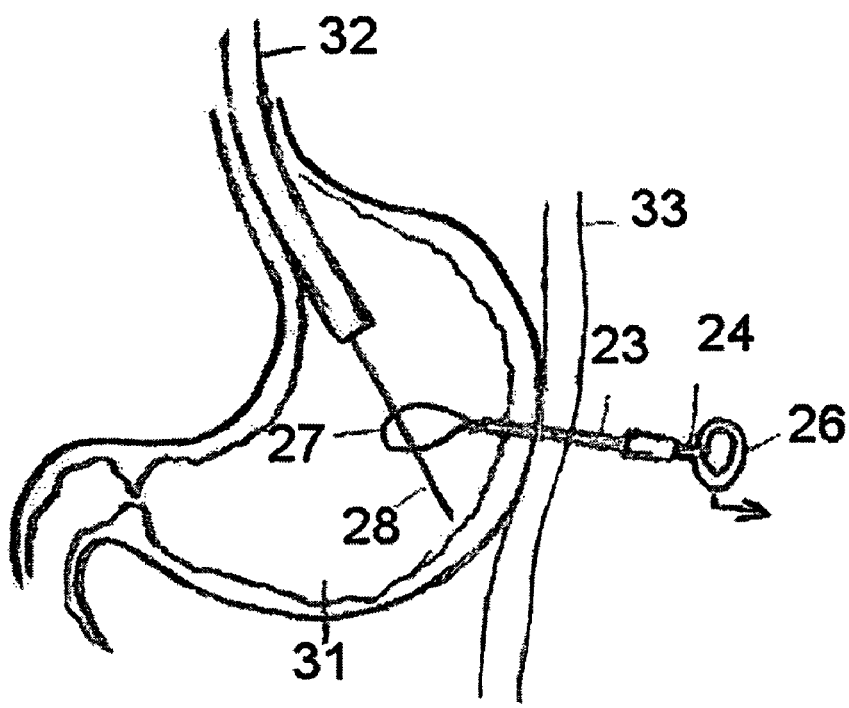
FIGS. 5A-5F sequentially illustrate the methodology for placing an ostomy tube using the wire-loop device, the ostomy tube device, and the tubular device of the present invention.

As can be seen in FIG. 5A (with further reference to FIGS. 4A-4C), an endoscope 32 is advanced into the lumen of a desired hollow organ 31, such as, stomach, in this example. Usually, endoscope is advanced to desired hollow organ through a natural body opening and natural tracts, as in illustrated case of stomach, through the mouth and the esophagus. In other applications, endoscope can be introduced also through artificial openings as gastrostomy, cecostomy, and ileostomy. The lumen of the hollow organ 31 is inflated with air for better visualization and manipulations. Under local or general anesthesia the first end 30 of the needle 23 is introduced into the lumen of the hollow organ 31 through the abdominal wall 33 while the second end of the needle 23 remains outside of abdominal wall 33. After the first end 30 of the needle 23 is visualized in the lumen of the hollow organ 31, the wire-loop 27 of wire-loop device 24 is passed through the needle 23 until wire-loop 27 completely extends from the first end 30 of the needle 23 and opens inside the lumen of the hollow organ 31. A second end of a flexible guide wire 28 is introduced in a working channel of the endoscope and is passed through until appears in the lumen of the hollow organ 31. At that point a first end (not shown on FIG. 5A) of the flexible guide wire 28 forming a loop remains extended from the working channel of endoscope outside of subject's body. Under endoscope visualization the second end of the flexible guide wire 28 is passed and positioned through open wire-loop 27. This step can be facilitated by positioning the endoscope 32 perpendicularly to plane of open wire-loop 27. Rotating the plane of open wire-loop 27 by means of the handle 26 remaining outside of subject's body can also help in this step.

Figure 5B:
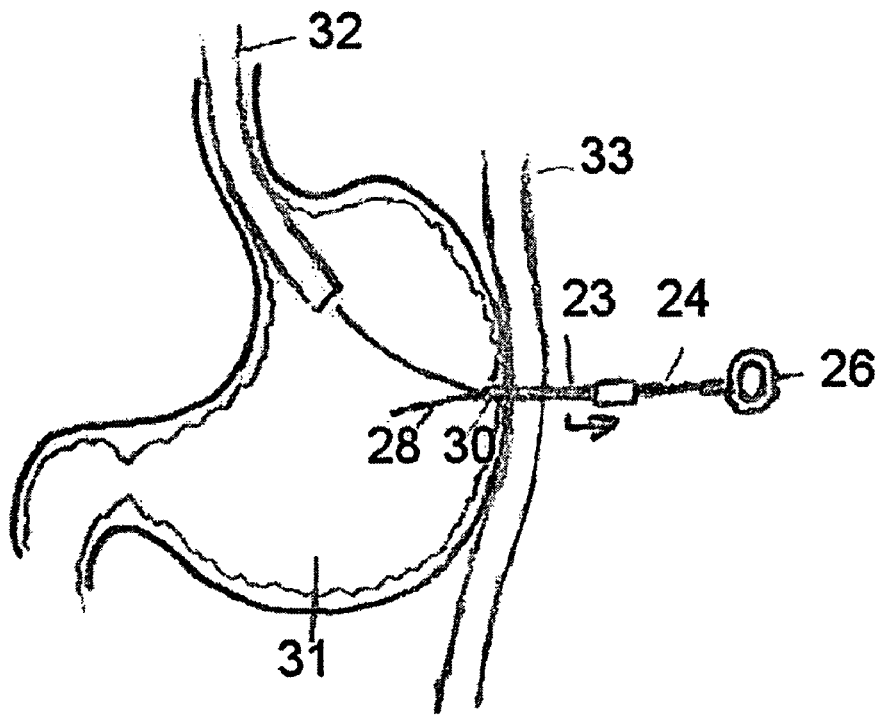

FIG. 5B shows the second end of flexible guide wire 28 grasped by the wire-loop devices 24 inside the lumen of the hollow organ 31. To do this, the handle 26 of the wire-loop device 24 is pulled away from the needle 23 pulling the wire-loop 27 inside the lumen of the needle 23 until flexible guide wire 28 is pressed against the first end 30 of the needle 23. While continuing grasping the flexible guide wire 28 in this manner, the wire-loop device 24 and the needle 23 are pulled together toward and through the hollow organ 31 wall and the abdominal wall 33. The second end of the flexible guide wire 28 bends over the wire-loop 27 and follows through the hollow organ 31 wall and the abdominal wall 33 outside the abdominal wall.

While retaining the second end of the flexible guide wire 28 in position outside the abdominal wall 33, the endoscope is withdrawn out of the body, leaving the first end of the flexible guide wire 28 extended out of the body natural opening, such as, mouth in this example.

Figure 5C:
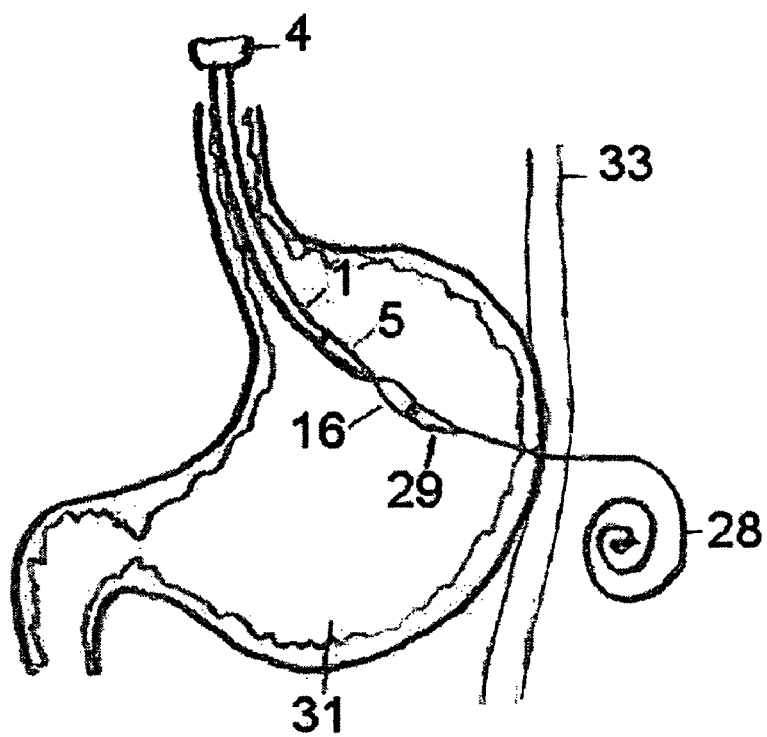

FIG. 5C illustrates an ostomy tube device comprising a hollow flexible tube 1 having a collapsible internal retaining member 4 secured at a first end, a tapered cannula 5 attached to a second end and a leading pole loop 16 attached and extended from a taper end of the tapered cannula 5. The leading pole loop 16 of the ostomy tube device is secured to the first end of the flexible guide wire 28 extended through the body opening, mouth. In preferred embodiment the first end of the flexible guide wire 28 forms a loop 29, thus, loop to loop coupling is used to secure the leading pole loop 16 of the ostomy tube device to first end of the flexible guide wire 28. When the second end of flexible guide wire 28 is pulled out of the abdominal wall 33, the ostomy tube device secured to the flexible guide wire 28 is pulled into the body opening and passes into the lumen of the hollow organ 31.

Figure 5D:
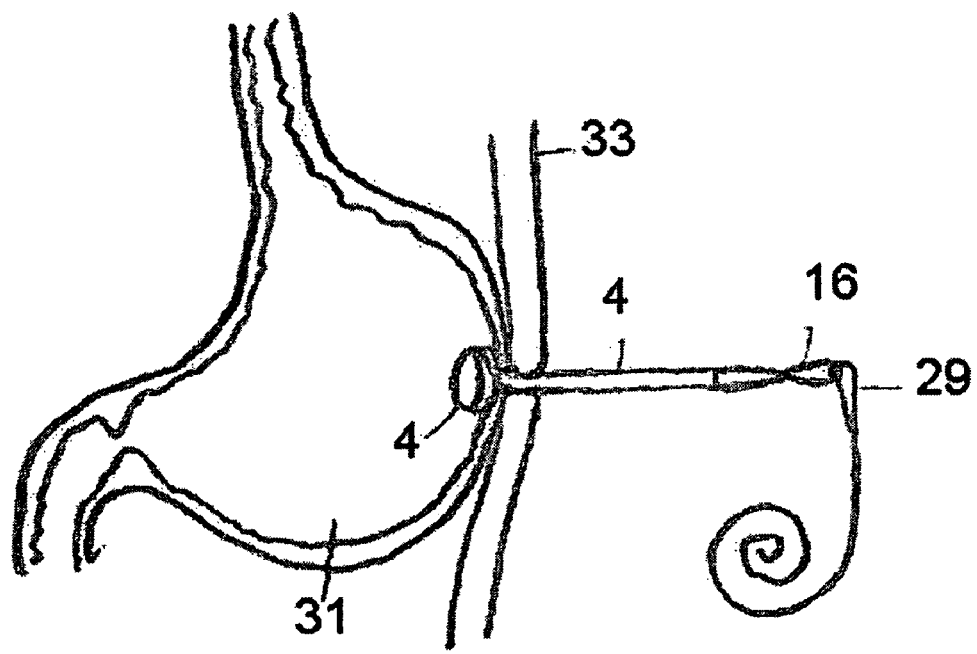

Pulling further the flexible guide wire 28 out of abdominal wall 33 will draw the leading pole loop 16 with attached the tapered cannula 5 and the hollow flexible tube 1 through hollow organ 31 wall and abdominal wall 33 out of the abdominal wall as depicted in FIG. 5D. At that point, the internal retention member 4 abuts against the inner surface of the hollow organ 13.

The method of an ostomy tube placement described above and illustrated in FIGS. 5A-5D with use of the wire-loop device 24, compared with the prior art, allows to improve technique, eliminating a step of passing the flexible guide wire through the needle in abdominal wall and lumen of hollow organ, and further out through natural body opening; eliminates a step of capturing of the flexible guide wire by a snare device introduced through the working channel of endoscope, requiring complex manipulation with the endoscope, the snare and cooperation with an assistant activating the snare; eliminates a step of engaging 150 cm long snare device through working channel of endoscope; eliminates a step of removing 150 cm long snare device out of working channel of endoscope; eliminates a need of using snare device or any other grasping device suitable for use through the endoscope, those devices are about 150 cm long, complex, and costly; eliminates a need of the assistant to help activate the snare device. In contrast with the snare device of the prior art, the wire-loop device 24 of present invention is simple and non costly; is small and requires less place for packaging; requires to be advanced only for about 15 cm; in best mode will be positioned inside the needle 23 by manufacturer and will requires to be advanced only for about 5-6 cm; is easy to be positioned and manipulated by a single person without help of the assistant.

In the method of an ostomy tube placement described above and illustrated in FIGS. 5A-5D the ostomy tube device of the present invention depicted in FIGS. 2A-2B and described in details above is used as preferred embodiment. However, any prior art ostomy tube device, as gastrostomy tube device, having a hollow flexible tube, an internal retaining member and a tapered cannula with a leading pole loop attached and extended from a taper end of the tapered cannula, can be alternatively used.

In another method of an ostomy tube placement, including all steps described above and illustrated in FIGS. 5A-5D, using the ostomy tube device of the present invention depicted in FIGS. 2A-2B and described in details above, the following steps are performed additionally: the hollow flexible tube 1 and the tapered cannula 5 are pulled apart, releasing the second end 3 of the hollow flexible tube 1 from the attachment with the pull-loop member 9 and the tapered cannula 5. Thus, use of the ostomy tube device of the present invention in the method of an ostomy tube placeman of the present invention eliminates the need of sharp devices such as scissors, knifes, cutting pliers to cut the hollow flexible tube 1 or a pull-loop member 9, to release said hollow flexible tube, as was done in the prior art.

Figure 5E:
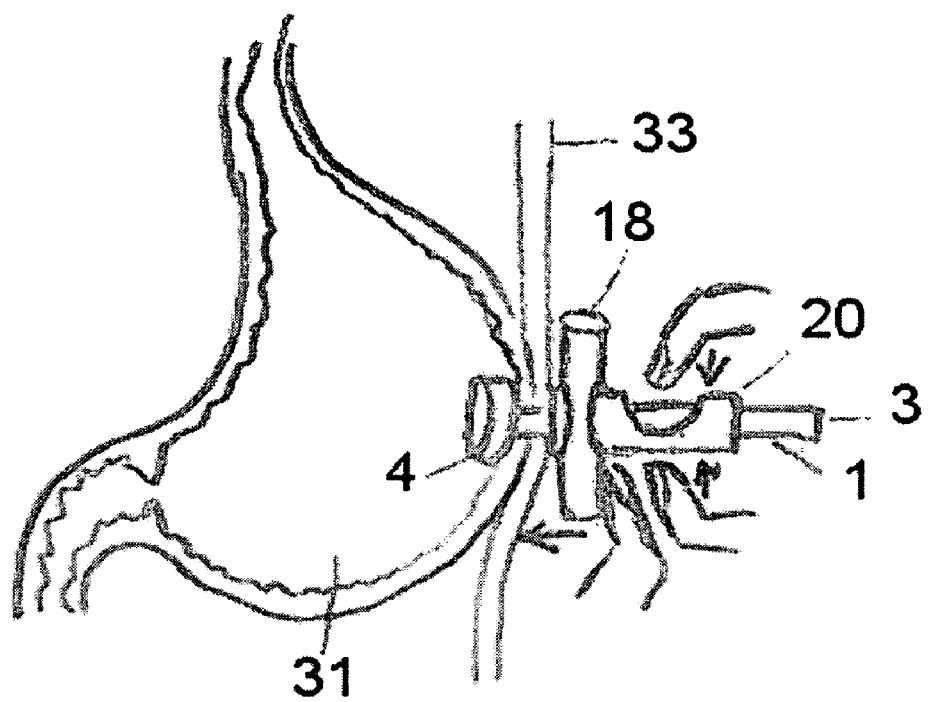

Turning to FIG. 5E (with further reference to FIGS. 3E-3F), the external retention member 18, positioned over the leading end of the tubular delivery means device 20, has been passed over the second end 3 of the hollow flexible tube 1, and further along said hallow hollow flexible tube 1 up to the abdominal wall 33 outer surface. The hollow flexible tube 1, passed trough the lumen of the tubular device 20, is held against the tubular device 20 by a finger through the additional opening 21 on the side of the tubular device. At that point, the external retention member 18 is removed from the tubular device 20 and is positioned over the hollow flexible tube 1 in elected place next to the abdominal wall 33 outer surface. The tubular device 20 freed from the external retention member 18 is pulled off the hollow flexible tube 1 in retrograde direction. Thus, the tubular device 20 allows to overcome difficulties of prior art techniques in passing external retention member over the end 3 and along the flexible hollow tube 1.

Figure 5F:
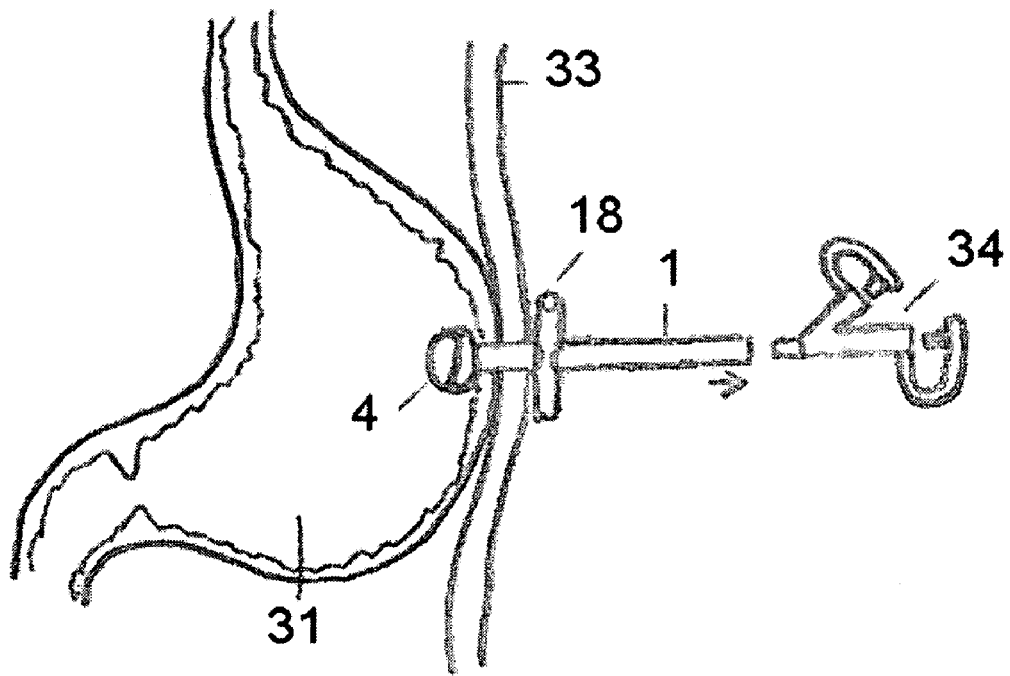

FIG. 5F shows the hollow flexible tube 1 positioned through the hollow organ 31 wall and the abdominal wall 33 with the internal retention member 4 abutting against the inner surface of the hollow organ 33, and the external retention member abutting against the abdominal wall 33 outer surface. A standard connecting union 34 is attached to the second end 3 of the hollow flexible tube 1 and is used for delivery of enteral nutrition, medications, and other fluids, or venting the hollow organ 33.

An ostomy placement kit, in accordance with the present invention, includes an ostomy tube device, an external retention member, a needle and a flexible guide wire. The ostomy tube device, included in this kit and depicted in FIG. 5C and FIG. 5D, comprise the hollow flexible tube 1 having the collapsible internal retaining member 4 secured at the first end, the tapered cannula 5 attached to the second end and the leading pole loop 16 attached and extended from the taper end of the tapered cannula 5. The external retention member 18 modifications of this kit, depicted in FIGS. 3a-3C, have the bore 19 about midportion sized to accommodate and frictionally retain the hollow flexible tube 1 of the ostomy tube device. The needle of this kit, depicted in FIG. 4A, has the first end 30 to be placed in the lumen of the hollow organ 31 through the abdominal wall 33, a second end to remain outside of the abdominal wall, and the lumen open at both ends. The flexible guide wire 28 of this kit, shown in FIG. 5C, has the first end forming the loop 29 and the second end. The flexible guide wire 28 is constructed from the flexible thread made either from a metal wire such as medical stainless steel wire, or from any synthetic polymer material such as nylon, or from natural materials such as silk, and their combinations. The length of the flexible guide wire 28 exceeds the length of used endoscope.

An alternative ostomy placement kit in addition to the ostomy tube device, the external retention member, the needle and the flexible guide wire includes a wire-loop device. The wire-loop device 24, included in this kit and shown in FIG. 4B, has the midportion rod 25 with the wire-loop 27 attached to one end and of the handle attached to the other end. The midportion rod 25 and the wire-loop 27 are sized in a diameter to be able to pass trough the lumen of the needle 23, as is shown on FIG. 4 C. Additionally, the midportion rod 25 is sized in length about the length of the needle 23 to allow the wire-loop 27 extend out of the first end 30 of the needle 23 when the midportion rode 24 is completely engaged in the lumen of the needle 23.

Another alternative ostomy placement kit in addition to the external retention member, the needle, the flexible guide wire and the wire-loop device includes the ostomy tube device of present invention. The ostomy tube device of present invention included in this kit as depicted in FIG. 2B comprise the hollow flexible tube 1 having the first end 2, the second end 3 and the lumen opened at both ends; the collapsible internal retention member 4 surrounding the first end 2 of the hollow flexible tube 1 and being secured thereto; the tapered cannula 5 having the wide portion ending by the wide end 8 and the tapered portion ending by the tapered end 6, and the lumen open on both ends; the lumen of the wide portion of said tapered cannula 5 is sized to accommodate folded and collapsed the second end 3 of the hollow flexible tube 1; the pull-loop member 9 having the leading pole loop 15 and the rear pole loop 16; the pull-loop member 9 is passed through the lumen of the tapered cannula so that the leading pole loop 15 extends from the tapered end 6 of the tapered cannula 5, and the rear pole loop 16 extends out of the wide portion of the tapered cannula 5 through the wide end 8; the second end 3 of the hollow flexible tube 1 is folded over the rear pole loop 16 and squeezed into the lumen 7 of the wide portion of the tapered cannula 5 pulled by the rear pole loop 16.

Yet another alternative ostomy placement kit in addition to the ostomy tube device, the external retention member, the needle, the flexible guide wire and the wire-loop device includes the tubular device for delivering the external retention member over the hollow flexible tube. The tubular device for delivering the external retention member included in this kit is constructed as a tube of about 3-5 cm from non collapsible, hard material having a leading end, a second end and a lumen opened at both ends. The diameter of the lumen of the tubular device is sized slightly bigger then the diameter of the hollow flexible tube 1 of the ostomy tube device. Preferably, the tubular device included in this kit already has the external retention member 18 positioned over its leading end.

In another alternative ostomy placement kit, including the ostomy tube device, the external retention member, the needle, the flexible guide wire, the wire-loop device, and the tubular device for delivering the external retention member over the hollow flexible tube, the tubular device 20 has an additional opening 21, communicating with the lumen of the tubular device 20, as depicted in FIG. 3D-3F. That additional opening 21 is big enough to accommodate a finger so that the finger will hold securely the hollow flexible tube 1, passed through the lumen of the tubular device 20, against the tubular device 20.

An alternative ostomy placement kit in addition to the ostomy tube device of present invention, as depicted in FIG. 2B, the external retention member, the needle, the flexible guide wire and the wire-loop device includes the tubular device for delivering the external retention member over the hollow flexible tube. The tubular device for the external retention member included in this kit is constructed as a tube of about 3-5 cm from non collapsible, hard material having a leading end, a second end and a lumen opened at both ends. The diameter of the lumen of the tubular device is sized slightly bigger then the diameter of the hollow flexible tube 1 of the ostomy tube device. Preferably, the tubular device included in this kit already has the external retention member 18 positioned over its leading end.

In another alternative ostomy placement kit including the ostomy tube device of present invention, as depicted in FIG. 2B, the external retention member, the needle, the flexible guide wire, the wire-loop device, and the tubular device for the external retention member, the tubular device 20 has an additional opening 21, communicating with the lumen of the tubular device 20, as depicted in FIG. 3D-3F. That additional opening 21 is big enough to accommodate a finger so that the finger will securely hold the hollow flexible tube 1, passed through the lumen of the tubular device 20, against the tubular device 20.

Yet another alternative ostomy placement kit in addition to the ostomy tube device, the external retention member, the needle and the flexible guide wire includes the tubular device for the external retention member. The tubular device for the external retention member included in this kit is constructed as a tube of about 3-5 cm from non collapsible, hard material having a leading end, a second end and a lumen opened at both ends. The diameter of the lumen of the tubular device is sized slightly bigger then the diameter of the hollow flexible tube 1 of the ostomy tube device. Preferably, the tubular device included in this kit already has the external retention member 18 positioned over its leading end.

In an alternative ostomy placement kit including the ostomy tube device, the external retention member, the needle, the flexible guide wire and the tubular device for the external retention member, the tubular device 20 has an additional opening 21, communicating with the lumen of the tubular device 20, as depicted in FIG. 3D-3F. That additional opening 21 is big enough to accommodate a finger so that the finger will hold securely the hollow flexible tube 1, passed through the lumen of the tubular device 20, against the tubular device 20.

Another alternative ostomy placement kit in addition to the external retention member, the needle, the flexible guide wire and the tubular device includes the ostomy tube device of present invention. The ostomy tube device of present invention included in this kit as depicted in FIG. 2B comprise the hollow flexible tube 1 having the first end 2, the second end 3 and the lumen opened at both ends; the collapsible internal retaining member 4 surrounding the first end 2 of the hollow flexible tube 1 and being secured thereto; the tapered cannula 5 having the wide portion ending by the wide end 8 and the tapered portion ending by the tapered end 6, and a lumen opened on both ends; the lumen of the wide portion of said tapered cannula 5 is sized to accommodate folded and collapsed the second end of the hollow flexible tube 1; the pull-loop member 9 having said leading pole loop 15 and a rear pole loop 16; the pull-loop member 9 is passed through the lumen of the tapered cannula so that the leading pole loop 15 extends from the tapered end 6 of the tapered cannula 5, and the rear pole loop 16 extends out of the wide portion of the tapered cannula 5 through the wide end 8; the second end 3 of the hollow flexible tube 1 is folded over the rear pole loop 16 and squeezed into the lumen 7 of the wide portion of the tapered cannula 5 pulled by the rear pole loop 16.

In one more alternative ostomy placement kit, including the ostomy tube device of present invention, as depicted in FIG. 2B, the external retention member, the needle, the flexible guide wire and the tubular device, the tubular device 20 has an additional opening 21, communicating with the lumen of the tubular delivery means 20 as depicted in FIG. 3D-3F. That additional opening 21 is big enough to accommodate a finger so that the finger will hold securely the hollow flexible tube 1, passed through the lumen of the tubular device 20, against the tubular device 20

Above described ostomy placement kits as in prior art are packaged in suitable container, sterilized and prepackaged in sterile sealed container.

INDUSTRIAL APPLICABILITY

The medical profession and enteral feeding industry has sought ways to simplify technique of ostomy placement, reduce time and manpower used, decrease the cost of ostomy kits, when possible eliminate use of sharp instruments. This invention solves these long-felt needs.

While the present invention has been described and illustrated in considerable detail with reference to certain preferred versions thereof, it is to be understood that numerous changes and modifications may be made therein, by those of ordinary skill in the art, without departing from the spirit and scope of the invention as defined in the appended claims.

What is claimed is:

1. An ostomy tube device, comprising:
  (a) a hollow flexible tube having a first end, a second end and a lumen opened at both said first end and said second end;
  (b) a collapsible internal retention member surrounding the first end of said hollow flexible tube and being secured thereto;
  (c) a tapered cannula having a wide portion ending by a wide end and a tapered portion ending by a tapered end, and a lumen open on both said tapered end and said wide end; said lumen of said wide portion of said tapered cannula is sized to accommodate folded and collapsed said second end of said hollow flexible tube;

(d) a pull-loop member constructed from a flexible thread having a leading pole loop at one pole and a rear pole loop at another pole; said pull-loop member being passed through the lumen of said tapered cannula so that said leading pole loop extends from said tapered end of said tapered cannula, and said rear pole loop extends out of said wide portion of said tapered cannula through said wide end, wherein said second end of said hollow flexible tube is positioned through said rear pole loop extending out of said wide portion of said tapered cannula through said wide end; pulling said tapered cannula and said leading pole loop apart pulls said rear pole loop into the lumen of said wide portion of said tapered cannula; said second end of said hollow flexible tube folds over said rear pole loop and squeezes into the lumen of said wide portion of said tapered cannula pulled by said rear pole loop to provide a secure and releasable attachment between said pull-loop member, said tapered cannula and said hollow flexible tube; said attachment is strong enough to overcome resistance forces on said ostomy tube device while it is pulled by said leading pole loop through a lumen and a wall of hollow organ and abdominal wall; said second end of said hollow flexible tube is easy to disengage from said attachment by simply pulling apart said hollow flexible tube and said tapered cannula, eliminating the need of sharp devices as scissors, knifes, cutting pliers to cut said hollow flexible tube or said pull-loop member to release said hollow flexible tube from the attachment with said tapered cannula and said pull-loop.

2. The ostomy tube device according to claim 1, wherein said pull-loop member is formed from said flexible thread having a midportion, a first end and a second end; said first and said second ends of said flexible thread of pull-loop member are fastened together forming a closed loop having the leading pole loop at one pole and the rear pole loop at another pole; said pull-loop member being passed through the lumen of said tapered cannula so that said leading pole loop extends from said tapered end of said tapered cannula, and said rear pole loop extends out of said wide portion of said tapered cannula through said wide end.

3. The ostomy tube device according to claim 1, wherein said pull-loop member is formed from said flexible thread having a midportion, a first end and a second end; said first end and said second end of said flexible thread of said pull-loop member are fastened to said midportion of said flexible thread separately and apart one from the other forming the leading pole loop and the rear pole loop, separated by a segment of said midportion of said flexible thread; said pull-loop member being passed through the lumen of said tapered cannula so that said leading pole loop extends from said tapered end of said tapered cannula and said rear pole loop extends out of said wide portion of said tapered cannula through said wide end.

4. The ostomy tube device according to claim 1, wherein said pull-loop member is formed from said flexible thread having a midportion, a first end and a second end; said first end and said second end of said flexible thread of said pull-loop member are fastened together and to said midportion of said flexible thread forming the leading pole loop and the rear loop; said pull-loop member being passed through the lumen of said tapered cannula so that said leading pole loop extends from said tapered end of said tapered cannula and said rear pole loop extends out of said wide portion of said tapered cannula through said wide end.

5. The ostomy tube device according to claim 1, wherein said pull-loop member is formed from said flexible thread having a midportion, a first end and a second end; said second end of said flexible thread of said pull-loop member being fastened to said midportion of said flexible thread forming the rear pole loop; said first end of said flexible thread of said pull loop member is imbedded into said tapered cannula; said pull-loop member being passed through the lumen of said tapered cannula so that said midportion of said flexible thread extends from said tapered end of said tapered cannula forming the leading pole loop and said rear pole loop extends out of said wide portion of said tapered cannula through said wide end.

6. The ostomy tube device according to claim 1, wherein said pull-loop member is formed from said flexible thread having a midportion, a first end and a second end; said first end of said flexible thread of said pull-loop member is fastened to said midportion of said flexible thread forming the leading pole loop; said second end of said flexible thread of said pull-loop member is imbedded into said tapered cannula; said pull-loop member being passed through the lumen of said tapered cannula so that said midportion of said flexible thread extends out of said wide portion of said tapered cannula through said wide end forming said rear pole loop and said leading pole loop extends out of said tapered portion of said tapered cannula through tapered end.

7. The ostomy tube device according to claim 1, wherein said pull-loop member is formed from said flexible thread having a midportion, a first end and a second end; said first end and said second end of said flexible thread of said pull-loop member are imbedded into said tapered cannula; said pull-loop member being passed through the lumen of said tapered cannula so that said midportion of said flexible thread extends from said tapered end of said tapered cannula forming the leading pole loop and extends out of said wide portion of said tapered cannula through said wide end forming said rear pole loop.

8. The ostomy tube device according to claim 1, wherein said pull-loop member is formed from said flexible thread constructed as O ring having the leading pole loop at one pole and the rear pole loop at another pole; said pull-loop member being passed through the lumen of said tapered cannula so that said leading pole loop extends from said tapered end of said tapered cannula, and said rear pole loop extends out of said wide portion of said tapered cannula through said wide end.

9. The ostomy tube device according to claim 1, wherein said flexible thread of said pull-loop member is constructed from a metal wire.

10. The ostomy tube device according to claim 1, wherein said flexible thread of said pull-loop member is constructed from synthetic polymer material.

11. An ostomy placement kit, comprising:
a. an ostomy tube device comprising a hollow flexible tube having a collapsible internal retention member secured at a first end and a tapered cannula attached to a second end; said tapered cannula having a leading pole loop attached to it and extended from a taper end of said tapered cannula; wherein
said hollow flexible tube having said first end, said second end and a lumen opened at both said first end and said second end;
said collapsible internal retention member surrounding the first end of said hollow flexible tube and being secured thereto;
said tapered cannula having a wide portion ending by a wide end and a tapered portion ending by said tapered end, and a lumen open on both said tapered end and said wide end; said lumen of said wide portion of said tapered cannula is sized to accommodate folded and collapsed said second end of said hollow flexible tube;

a pull-loop member having said leading pole loop at one pole and a rear pole loop at another pole; said pull-loop member being passed through the lumen of said tapered cannula so that said leading pole loop extends from said tapered end of said tapered cannula, and said rear pole loop extends out of said wide portion of said tapered cannula through said wide end; said second end of said hollow flexible tube is positioned through said rear pole loop extending out of said wide portion of said tapered cannula through said wide end; pulling said tapered cannula and said leading pole loop apart pulls said rear pole loop into the lumen of said wide portion of said tapered cannula; said second end of said hollow flexible tube folds over said rear pole loop and squeezes into the lumen of said wide portion of said tapered cannula pulled by said rear pole loop, whereby providing a secure and releasable attachment between said pull-loop member, said tapered cannula and said hollow flexible tube; said attachment is strong enough to overcome resistance forces on said ostomy tube device while it is pulled by said leading pole loop through the lumen and the wall of hollow organ and the abdominal wall; said second end of said hollow flexible tube is easy to disengage from said attachment by simply pulling apart said hollow flexible tube and said tapered cannula, eliminating the need of sharp devices such as scissors, knifes, cutting pliers to cut said hollow flexible tube or said pull-loop member to release said hollow flexible tube from the attachment with said tapered cannula and said pull-loop member;

b. an external retention member having a bore at about midportion; said bore is sized to accommodate and frictionally retain said hollow flexible tube of said ostomy tube device;

c. a needle having a first end to be placed in a lumen of a hollow organ through an abdominal wall, a second end to remain outside of said abdominal wall, and a lumen opened at both ends;

d. a flexible guide wire having a first end, forming a loop, and a second end;

e. a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body.

12. The ostomy placement kit according to claim 11, including a tubular device made from non collapsible, hard material having a leading end, a second end and a lumen opened at both said leading end and said second end; the diameter of said lumen of said tubular device is sized slightly bigger then the diameter of said hollow flexible tube of said ostomy tube device; said leading end of said tubular device is pushed through the bore of said external retention member, so that said external retention member is positioned at about the leading end of said tubular device, whereby said external retention member positioned over the leading end of said tubular device is passed without resistance over the second end of said hollow flexible tube of said ostomy tube device and further along said hollow flexible tube, and is removed from said tubular device and positioned over said hollow flexible tube in elected place close to the abdominal wall outer surfaces.

13. The ostomy placement kit according to claim 12, wherein said tubular device has an additional opening on a side between said leading end and said second end; said additional opening communicates with said lumen of said tubular device; said additional opening is big enough to accommodate a finger so that said finger will hold securely said hollow flexible tube, passed through the lumen of said tubular delivery, against said tubular device, whereby said tubular delivery will remain in elected place along said hollow flexible tube while said external retention member is removed from said tubular device.

14. An ostomy placement kit, comprising:

a. an ostomy tube device comprising a hollow flexible tube having a collapsible internal retention member secured at a first end and a tapered cannula attached to a second end; said tapered cannula having a leading pole loop attached to it and extended from a taper end of said tapered cannula;

b. an external retention member having a bore at about midportion; said bore is sized to accommodate and frictionally retain said hollow flexible tube of said ostomy tube device;

c. a needle having a first end to be placed in a lumen of a hollow organ through an abdominal wall, a second end to remain outside of said abdominal wall, and a lumen opened at both ends;

d. a flexible guide wire having a first end, forming a loop, and a second end;

e. a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body;

f. a tubular device made from non collapsible, hard material having a leading end, a second end and a lumen opened at both said leading end and said second end; the diameter of said lumen of said tubular device is sized slightly bigger then the diameter of said hollow flexible tube of said ostomy tube device; said leading end of said tubular device is pushed through the bore of said external retention member, so that said external retention member is positioned at about the leading end of said tubular device, whereby said external retention member positioned over the leading end of said tubular device is passed without resistance over the second end of said hollow flexible tube of said ostomy tube device and further along said hollow flexible tube, and is removed from said tubular device and positioned over said hollow flexible tube in elected place close to the abdominal wall outer surfaces.

15. The ostomy placement kit according to claim 14, wherein said tubular device has an additional opening on a side between said leading end and said second end; said additional opening communicates with said lumen of said tubular device; said additional opening is big enough to accommodate a finger so that said finger will hold securely said hollow flexible tube, passed through the lumen of said tubular device, against said tubular device, whereby said tubular device will remain in elected place along said hollow flexible tube while said external retention member is removed from said tubular device.

16. An ostomy placement kit, comprising:
   a. an ostomy tube device comprising a hollow flexible tube having a collapsible internal retention member secured at a first end and a tapered cannula attached to a second end; said tapered cannula having a leading pole loop attached to it and extended from a taper end of said tapered cannula;
   b. an external retention member having a bore at about midportion; said bore is sized to accommodate and frictionally retain said hollow flexible tube of said ostomy tube device;
   c. a needle having a first end to be placed in a lumen of a hollow organ through an abdominal wall, a second end to remain outside of said abdominal wall, and a lumen opened at both ends;
   d. a flexible guide wire having a first end, forming a loop, and a second end;
further including a tubular device made from non collapsible, hard material having a leading end, a second end and a lumen opened at both said leading end and said second end; the diameter of said lumen of said tubular device is sized slightly bigger then the diameter of said hollow flexible tube of said ostomy tube device; said leading end of said tubular device is pushed through the bore of said external retention member, so that said external retention member is positioned at about the leading end of said tubular delivery, whereby said external retention member positioned over the leading end of said tubular device is passed without resistance over the second end of said hollow flexible tube of said ostomy tube device and further along said hollow flexible tube, and is removed from said tubular device and positioned over said hollow flexible tube in elected place close to abdominal wall outer surfaces.

17. The ostomy placement kit according to claim 16, wherein said tubular device has an additional opening on a side between said leading end and said second end; said additional opening communicates with said lumen of said tubular delivery; said additional opening is big enough to accommodate a finger so that said finger will hold securely said hollow flexible tube, passed through the lumen of said tubular device, against said tubular device, whereby said tubular device will remain in elected place along said hollow flexible tube while said external retention member is removed from said tubular delivery.

18. The ostomy placement kit according to claim 17, including a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body.

19. The ostomy placement kit according to claim 16, wherein said ostomy tube device comprises
   (a) said hollow flexible tube having said first end, said second end and a lumen opened at both said first end and said second end;
   (b) said collapsible internal retention member surrounding the first end of said hollow flexible tube and being secured thereto;
   (c) said tapered cannula having a wide portion ending by a wide end, a tapered portion ending by said tapered end and a lumen opened on both said tapered end and said wide end; said lumen of said wide portion of said tapered cannula is sized to accommodate folded and collapsed said second end of said hollow flexible tube;
   (d) a pull-loop member having said leading pole loop at one pole and a rear pole loop at another pole; said pull-loop member is passed through the lumen of said tapered cannula so that said leading pole loop extends from said tapered end of said tapered cannula, and said rear pole loop extends out of said wide portion of said tapered cannula through said wide end; said second end of said hollow flexible tube is positioned through said rear pole loop extending out of said wide portion of said tapered cannula through said wide end; pulling said tapered cannula and said leading pole loop apart pulls said rear pole loop into the lumen of said wide portion of said tapered cannula; said second end of said hollow flexible tube folds over said rear pole loop and squeezes into the lumen of said wide portion of said tapered cannula pulled by said rear pole loop, whereby providing a secure and releasable attachment between said pull-loop member, said tapered cannula and said hollow flexible tube; said attachment is strong enough to overcome resistance forces on said ostomy tube device while it is pulled by said leading pole loop through the lumen and the wall of the hollow organ and the abdominal wall; said second end of said hollow flexible tube is easy to disengage from said attachment by simply pulling apart said hollow flexible tube and said tapered cannula, eliminating the need of sharp devices such as scissors, knifes, cutting pliers to cut said hollow flexible tube or said pull-loop member to release said hollow flexible tube from the attachment with said tapered cannula and said pull-loop member.

20. The ostomy placement kit according to claim 19, including a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body.

21. The ostomy placement kit according to claim 19, wherein said tubular device has an additional opening on a side between said leading end and said second end; said additional opening communicates with said lumen of said tubular device; said additional opening is big enough to accommodate a finger so that said finger will hold securely said hollow flexible tube, passed through the lumen of said tubular device, against said tubular device, whereby said tubular delivery will remain in elected place along said hollow flexible tube while said external retention member is removed from said tubular device.

22. The ostomy placement kit according to claim 21, including a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body.

23. The ostomy placement kit according to claim 16, including a wire-loop device having a midportion rod, a wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device extend out of the first end of said needle when said midportion rod is engaged in the lumen of said needle, whereby the wire-loop of said wire-loop device can be passed through the lumen of the needle placed through the abdominal wall into the lumen of the hollow organ; the wire-loop of said wire-loop device can grasp the end of said flexible guide wire within the lumen of the hollow organ and pull said end of said flexible guide wire through the hollow organ and the abdominal wall out of body.

24. A method for an ostomy tube placement, comprising the steps of:
  (i) advancing an endoscope through a body opening into a lumen of a desired hollow organ,
  (ii) introducing a first end of a needle into the lumen of said desired hollow organ through an abdominal wall and a wall of said hollow organ, while leaving a second end of said needle outside of said abdominal wall,
  (iii) passing a wire-loop of a wire-loop device through the needle so that the wire-loop extends from the first end of the needle and opens in the lumen of said hollow organ, said wire-loop device having a midportion rod, said wire-loop attached to one end of said midportion rod and a handle attached to the other end of said midportion rod; said midportion rod and said wire-loop are sized in a diameter to be able to pass through the lumen of said needle; said midportion rod is sized in length about a length of said needle to allow said wire-loop of said wire-loop device to extend out of the first end of said needle when said midportion rod is engaged in the lumen of said needle,
  (iv) passing a second end of a flexible guide wire through the endoscope into the lumen of said desired hollow organ, said flexible guide wire having a first end forming a loop and the second end,
  (v) positioning the second end of the flexible guide wire through the wire-loop of the wire-loop device,
  (vi) grasping the second end of the flexible guide wire by the wire-loop of said wire-loop device,
  (vii) pulling the second end of the flexible guide wire grasped by the wire-loop from the lumen of the hollow organ, toward and through the hollow organ wall and the abdominal wall outside the abdominal wall,
  (viii) withdrawing the endoscope out of the body opening while retaining the second end of the flexible guide wire in position outside the abdominal wall and leaving the first end of the flexible guide wire extending out of said body opening,
  (ix) securing the first end of the flexible guide wire to a leading pole loop of an ostomy tube device, said ostomy tube device comprising a hollow flexible tube having a collapsible internal retention member secured at a first end, and a tapered cannula attached to a second end; said tapered cannula having said leading pole loop attached to it and extended from a taper end of said tapered cannula
  (x) passing the ostomy tube device through the body opening, the lumen and the hollow organ wall, and the abdominal wall by pulling the flexible guide wire by the second end until the leading pole loop with the attached tapered cannula and the hollow flexible tube extend out of the abdominal wall and said collapsible internal retention member abuts against the inner surface of the hollow organ,
  (xi) releasing the second end of the hollow flexible tube from the attachment between the leading pole loop, the hollow flexible tube, and the tapered cannula by pulling apart said hollow flexible tube and said tapered cannula of said ostomy tube device, said ostomy tube device comprises:
    (a) said hollow flexible tube having said first end, said second end and a lumen opened at both said first end and said second end;
    (b) said collapsible internal retention member surrounding the first end of said hollow flexible tube and being secured thereto;
    (c) said tapered cannula having a wide portion ending by a wide end and a tapered portion ending by said tapered end, and a lumen open on both said tapered end and said wide end; said lumen of said wide portion of said tapered cannula is sized to accommodate folded and collapsed said second end of said hollow flexible tube;
    (d) a pull-loop member having said leading pole loop at one pole and a rear pole loop at another pole; said pull-loop member passed through the lumen of said tapered cannula so that said leading pole loop extends from said tapered end of said tapered cannula, and said rear pole loop extends out of said wide portion of said tapered cannula through said wide end; said second end of said hollow flexible tube is positioned through said rear pole loop extending out of said wide portion of said tapered cannula through said wide end; pulling said tapered cannula and said leading pole loop apart pulls said rear pole loop into the lumen of said wide portion of said tapered cannula; said second end of said hollow flexible tube folds over said rear pole loop and squeezes into the lumen of said wide portion of said tapered cannula pulled by said rear pole loop, whereby providing a secure and releasable attachment between said pull-loop member, said tapered cannula and said hollow flexible tube; said attachment is strong enough to overcome resistance forces on said ostomy tube device while it is pulled by said leading pole loop through the lumen and the wall of the hollow organ and the abdominal wall; said second end of said hollow flexible tube is easy to disengage from said attachment by simply pulling apart said hollow flexible tube and said tapered cannula, eliminating the need of sharp devices such as scissors, knifes, cutting pliers to cut said hollow flexible tube or said pull-loop member to release said hollow flexible tube from the attachment with said tapered cannula and said pull-loop is member.

25. The method for an ostomy tube placement as recited in claim 24, comprising the further steps of:
(i) passing an external retention member positioned over a leading end of a tubular device over the second end of said hollow flexible tube of said ostomy tube device and further along said hollow flexible tube up to the abdominal wall outer surface, said tubular device for the external retention member made from non collapsible, hard material having said leading end, a second end and a lumen opened at both said leading end and said second end; the diameter of said lumen of said tubular device is sized slightly bigger then the diameter of said hollow flexible tube of said ostomy tube device; said leading end of said tubular device is pushed through the bore of said external retention member, so that said external retention member is positioned at about the leading end of said tubular device, whereby said external retention member positioned over the leading end of said tubular device is passed without resistance over the second end of said hollow flexible tube of said ostomy tube device and further along said hollow flexible tube,
(ii) holding said hollow flexible tube, passed through the lumen of said tubular device against said tubular device by a finger through an additional opening on a side of said tubular device while removing the external retention member from said tubular device and positioning over said hollow flexible tube in elected place next to and abutting against the abdominal wall outer surface, said tubular device has said additional opening on the side between said leading end and said second end; said additional opening communicates with said lumen of said tubular device; said additional opening is big enough to accommodate a finger so that said finger will hold securely said hollow flexible tube passed through the lumen of said tubular device against said tubular device, whereby said tubular device will remain in elected place along said hollow flexible tube while said external retention member is removed from said tubular device,
(iii) pulling off the tubular device from the hollow flexible tube.

26. An ostomy tube device, comprising:
(a) a hollow flexible tube having a first end, a second end and a lumen opened at both said first end and said second end;
(b) a tapered cannula having a wide portion ending by a wide end and a tapered portion ending by a tapered end, and a lumen open on both said tapered end and said wide end; said lumen of said wide portion of said tapered cannula is sized to accommodate folded and collapsed said second end of said hollow flexible tube;
(c) a pull-loop member having a leading pole and a rear pole, and forming a rear pole loop at said rear pole; said pull-loop member is passed through the lumen of said tapered canula so that said leading pole extends from said tapered end of said tapered cannula, and said rear pole loop extends out of said wide portion of said tapered cannula through said wide end; said second end of said hollow flexible tube is positioned through said rear pole loop extending out of said wide portion of said tapered cannula through said wide end; pulling apart said tapered cannula and said pull-loop member extending through said tapered end of said tapered cannula pulls said rear pole loop into the lumen of said wide portion of said tapered cannula; said second end of said hollow flexible tube folds over said rear pole loop of said pull-loop member and squeezes into the lumen of said wide portion of said tapered cannula pulled by said rear pole loop, whereby providing a secure and releasable attachment between said pull-loop member, said tapered cannula and said hollow flexible tube; said attachment is strong enough to overcome resistance forces on said ostomy tube device while it is pulled by said pull-loop member through a lumen and a wall of hollow organ and abdominal wall; said second end of said hollow flexible tube is easy to disengage from said attachment by simply pulling apart said hollow flexible tube and said tapered cannula, eliminating the need of sharp devices as scissors, knifes, cutting pliers to cut said hollow flexible tube or said pull-loop member to release said hollow flexible tube from the attachment with said tapered cannula and said pull-loop member.

* * * * *